United States Patent [19]

Martin

[11] 4,231,359
[45] Nov. 4, 1980

[54] PERSONAL EMERGENCY BREATHING HOOD WITH NOSE BLOCKING DEVICE

[75] Inventor: Frank E. Martin, Chester, Md.

[73] Assignee: Midori Anzen Company, Ltd., Tokyo, Japan

[21] Appl. No.: 958,445

[22] Filed: Nov. 7, 1978

Related U.S. Application Data

[62] Division of Ser. No. 828,164, Aug. 23, 1977, abandoned.

[51] Int. Cl.³ .............................................. A62B 7/00
[52] U.S. Cl. .......................... 128/201.18; 128/201.23; 128/205.17; 128/206.29
[58] Field of Search ............... 128/142.7, 142.6, 142.5, 128/142 R, 145 A, 140 N, 140 R, 146.6, 147, 202, 191 R, 201.23, 205.17, 206.29, 201.18

[56] References Cited

U.S. PATENT DOCUMENTS

| 958,569 | 5/1910 | Venner | 128/140 N |
| 2,448,021 | 8/1948 | DeGrazia | 128/142.7 X |
| 3,521,629 | 7/1970 | Reynolds | 128/142.7 |
| 4,154,235 | 5/1979 | Warcke | 128/142.7 |

Primary Examiner—Henry J. Recla
Attorney, Agent, or Firm—Wenderoth, Lind & Ponack

[57] ABSTRACT

An emergency breathing hood for use with a breathing apparatus has a plastic hood made of a gas-impermeable, flame-resistant and transparent plastic film for covering the head of the wearer, a mouthpiece secured to and extending through the plastic hood, for providing a connection between the wearer's mouth and the breathing apparatus, and a nose blocking device for blocking the gas inflow into the nostrils and inhibiting outflow from the nostrils of the user, the nose blocking device being a cylindrically shaped device supported within the hood so that the cylindrically shaped device is positioned in front of and in contact with the wearer's nostrils when the hood is worn, and a thin elastic material over the cylindrically shaped device and extending over an area effective for covering the wearer's nostrils.

3 Claims, 3 Drawing Figures

PERSONAL EMERGENCY BREATHING HOOD WITH NOSE BLOCKING DEVICE

This application is a division of Ser. No. 828,164, filed Aug. 23, 1977, now abandoned.

BACKGROUND OF THE INVENTION

This invention relates to a personal emergency breathing hood with a nose blocking device.

DESCRIPTION OF THE PRIOR ART

In the event of a fire, a factory accident, a coal mine accident or an oxygen deficiency accident, an antitoxic mask is not effective for protecting the user. To provide a personal breathing apparatus effective under such circumstances, various types of breathing apparatuses comprising a self-contained oxygen source have been proposed.

Such breathing apparatuses utilize either a breathing mask system wherein respiration is accomplished through a mask hermetically enveloping the mouth and the nostrils of the wearer by intimately contacting the face, or a mouthpiece system wherein the respiration is through a mouthpiece held in the user's mouth.

The breathing mask system has a long history and many breathing masks have been proposed. However, these masks are large and heavy, not comfortable to wear and often require considerable time to put on. In particular, masks with means for protecting the eyes and facial skin are especially heavy and large, and uncomfortable to wear. Since the breathing mask is used under emergency circumstances and is usually used with an oxygen supply source and an exhaled gas purificating system which are always relatively heavy and large and complex, there has been a great demand for a breathing mouthpiece which is light in weight and easy to handle.

The mouthpiece system, on the other hand, is simple and light in weight since it supplies breathable gas to the user whose face is exposed to the atmosphere. However, for the same reasons that it is light and simple, it is completely ineffective for protecting the user's face.

Also, the mouthpiece system must be used together with some means for closing the nostrils of the user because the mouthpiece itself includes no nose closing device. Conventional nose closing devices are nose clips which exert force simultaneously on both sides of the nose to flatten the nostrils to the point of occlusion. Most nose clips are spring loaded to effect occlusion while others achieve the same effect by an adjustable clutch arrangement. Another type of conventional nose closing device is nose plugs which are inserted into the nostrils. All these conventional nose closing devices are disadvantageous in that the user always suffers from pain or at least feels uncomfortable when these nose blocking devices are in use. In some cases, the user feels the pain or discomfort points at his nose even after the nose closing device has been removed. Therefore, for the above reasons, the mouthpiece system has always been disliked by the user. This is particularly true for a new user who is not trained to wear the system.

SUMMARY OF THE INVENTION

Accordingly, an object of the present invention is to provide an emergency breathing hood having a new and improved nose blocking device and capable of being easily and quickly put on and comfortably worn.

Another object of the present invention is to provide an emergency breathing hood having a new and improved nose blocking device which is light in weight, has a simple structure, and which can be quickly, easily and comfortably put on and worn, and yet which still protects the face of the wearer against a hostile environment.

The emergency breathing hood according to the present invention comprises a plastic hood in the form of a bag having an opening for passing the wearer's head therethrough. The hood is made of a gas-impermeable, flame-resistant, transparent plastic film for covering the head against hostile environments. A mouthpiece is secured to and extends through the plastic hood so as to provide a connection between the wearer's mouth and the breathing apparatus. A nose blocking device is attached to the inner surface of the plastic hood. The nose blocking device comprises a cylindrically shaped device covered with a thin elastic material to provide a closure for closing the wearer's nostrils to prevent gas inflow through the nostrils and inhibiting outflow. The nose blocking device may preferably be attached to the plastic hood by a piece of elastic cord.

BRIEF DESCRIPTION OF THE DRAWINGS

The invention will now be described in conjunction with the preferred embodiments of the present invention shown in the accompanying drawings, in which.

DESCRIPTION OF THE PREFERRED EMBODIMENTS

Figure 1:
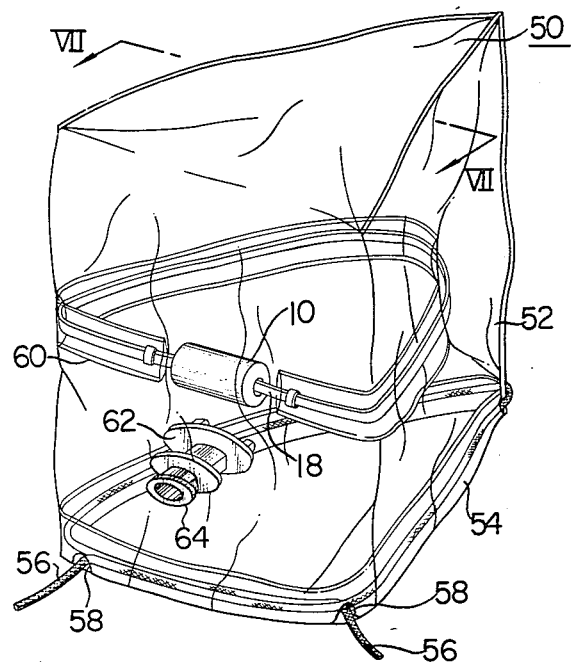
FIG. 1 is a perspective view of an emergency breathing hood having a nose blocking device according to the present invention.

Referring now to the Figures, an emergency breathing hood generally designated by the reference numeral 50 into which a nose blocking device is incorporated, comprises a thin, flexible, transparent plastic hood 52 formed into a bag having an opening for allowing the head to pass therethrough. The lower edge or the edge defining the opening of the plastic hood 52 is folded along the edge and secured to the hood to form a circumferential folded portion 54 defining therein an elongated circumferential space through which a piece of cord 56 slidably extends. The cord 56 is of inelastic material and its opposite ends extend outward through a pair of openings 58 formed in the folded portion 54. The cord 56 may be replaced by an elastic rubber cord if desired.

Figure 3:
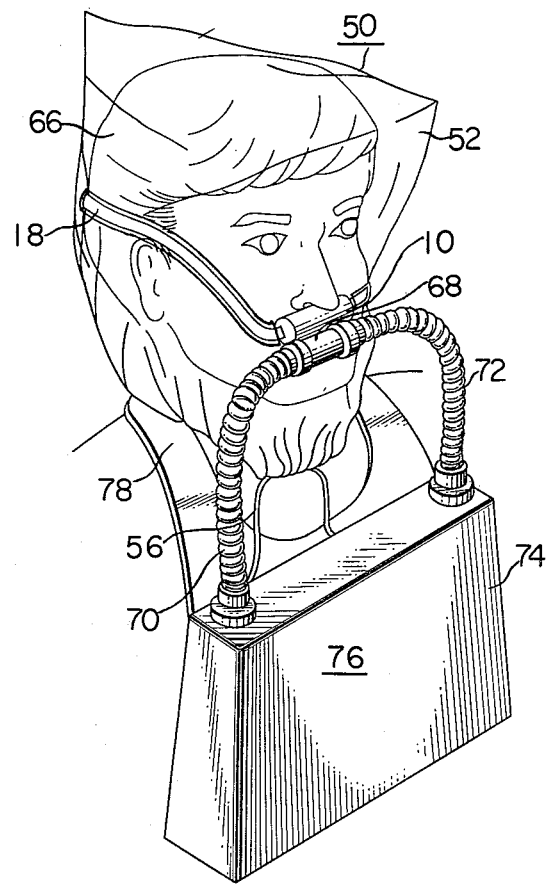
FIG. 3 is a view showing the emergency breathing hood of the present invention in use.
Figure 2:
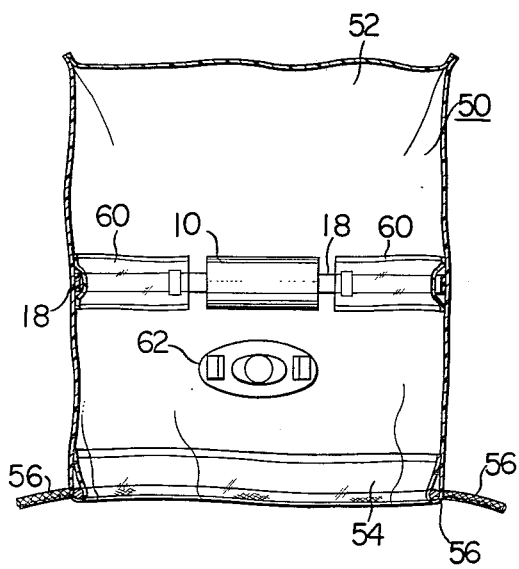
FIG. 2 is a sectional view taken along the line II—II of FIG. 1 and showing the front half of the hood as seen from the back of the hood with the rear half removed.

The plastic hood 52 illustrated in FIGS. 1-3 is made of flame-resistant transparent plastic film. However, the entire hood 52 is not always necessarily transparent; it is only the portion corresponding to the eyes when the hood is worn that must be transparent. Therefore, other portions of the plastic hood 52 may be made opaque or translucent by a reinforcement treatment, flame-resistivity treatment, coating treatment for irradiated heat reflection, etc., without any ill effects.

The preferable plastic materials for the plastic hood 52 include polyvinyl chloride film, a film of any of the teflon resins and a film of any of the polyimide resins. Other materials which are flammable can be properly used when a flame-resistant agent is added or a flame-resistant coating is applied. Flame-resistivity may preferably be such that the material does not burn when contacted by a flame or a match, or that the material does burn but rather self-extinguishes when the flame of the match is removed.

The plastic hood 52 has on its inner surface a nose block 10 for blocking the nostrils of the wearer when the hood is worn. The nose block 10 illustrated in the Figures is disclosed more fully hereinafter. The nose blocking device 10 has attached thereto a piece of elastic cord 18 such as rubber cord which is slidably disposed in the inner surface of the plastic hood 52 by means of a transparent plastic strip 60, attached at both its side edges to the inner surface of the hood 52 and defining therein an elongated space through which the elastic cord 18 slidably extends so as to allow the cord 18 to stretch when the nose block is worn. When desired, the elastic cord 18 may be directly secured to the hood 52. The elastic cord 18 also serves to support the hood 52 in the proper position with respect to the head. When the hood is worn, the elastic cord 18 is placed around the back of the head and the nose block 10 is elastically supported at the wearer's nostrils.

The emergency breathing hood 50 further comprises a mouthpiece 62 hermetically secured to the plastic hood 52 through an opening at the location corresponding to the location of the mouth when the hood 50 is worn. The mouthpiece 62 may be any conventional mouthpiece, of the type in which the inner or mouth end is inserted into and held in the mouth of the wearer and the outer end 64 extending outward from the plastic hood 52 is arranged to be connected to a check valve of the external breathing apparatus which will be described in more detail later on.

FIG. 3 illustrates the emergency breathing hood 50 worn by the wearer for breathing. The head of the wearer 66 is completely covered by the transparent plastic hood 52, and substantially isolated from the atmosphere by means of the neck strap 56 which has been pulled tight around the neck to close the opening of the hood 52. The elastic cord 18 for supporting the nose block 10 is stretched around the head and the nose block 10 is placed at the nostrils. Thus the nose block 10 is elastically supported at the nostrils. The mouthpiece 62 secured to the plastic hood 52 is inserted and held in the mouth. The outer end 64 of the mouthpiece 62 is coupled, through a check valve 68, to an inhalation hose 70 and an exhalation hose 72 each connected to the breathing bag 74 of the breathing apparatus 76 supported at the wearer's chest by a shoulder strap 78.

The nose blocking device 10 of the present invention comprises a cylindrically shaped device covered with a thin elastic material to provide closure for the nostrils. A particular embodiment which can be used has the cylindrically shaped device in the form of a substantially cylindrical block of relatively soft polyurethane material. Placed over the block is a thin, soft, flexible and gas-impermeable film. To the block can be attached the elastic straps 18 such as rubber bands to be placed behind the ears, or a single large loop to be placed around the wearer's head to elastically support the nose blocking device 10 in front of the nostrils of the wearer.

Material suitable for the gas-impermeable flexible film includes polyethylene, polyvinylidene chloride, natural rubber and synthetic rubber. Alternatively, a film of soft woven or unwoven material coated with any one of the abovementioned gas-impermeable materials is also suitable.

The cylindrical film placed over the block is supported in front of the wearer's nostrils so as to cover them by the elastic support strap 18. Upon exhalation, the nose blocking device inhibits exhalation through the nostrils but does not completely prevent it. Upon inhalation, however, the flexible film on the block deflects toward the nostrils and closes them due to the lower pressure between the nostrils and the film, thus blocking the nostrils to prevent the inhalation through the nostrils. Since the film is soft and flexible, and is stretched over the cylindrical surfaces of the block, the wearer only feels very light, not uncomfortable pressure.

As is apparent from the foregoing description of the invention, the emergency breathing hood of the present invention is advantageous in many respects over the prior art devices. Some of the advantages of the emergency breathing hood of the invention are:

(1) That the emergency breathing hood is extremely light in weight and capable of being very comfortably worn;

(2) That the hood can be folded into a very compact size, contributing to ease and convenience of storing when not in use;

(3) That the hood can be very easily, rapidly and properly donned by merely putting on the hood, pulling the neck strap, inserting the mouthpiece into the mouth and applying the nose block to the nostrils (when an elastic cord in substituted for the neck strap, this procedure is further simplified);

(4) That the hood completely covers the head for desirable facial protection, such as protection of the eyes, facial and cranium skin against sparks, smoke, dust or any irritating gas;

(5) That the emergency breathing hood is provided with the nose block effective for blocking the nostrils, so that the wearer is prevented from inhaling any hostile environment atmosphere and is inhibited from exhaling outside the closed circuit gas breathing apparatus, but allows such exhalation when necessary; and (6) That the emergency breathing hood can be comfortably worn because of its light weight and simple nose block as well as its wide field of view and capability of voice communication and also because the hood does not require a full hermetic seal around the neck or on the face due to the nose block.

What is claimed is:

1. An emergency breathing hood for use with a breathing apparatus, comprising:

a plastic hood made of a gas-impermeable, flame-resistant and transparent plastic film for covering the head of a wearer and including means for substantially sealing the hood around the neck of a wearer;

a mouthpiece secured to and extending through said plastic hood, for providing a connection between the wearer's mouth and the breathing apparatus; and a nose blocking device for blocking the gas inflow into the nostrils and inhibiting outflow from the nostrils of the user, said nose blocking device comprising a cylindrically shaped device supported within said hood so that said cylindrically shaped device is positioned in front of and in contact with the wearer's nostrils when said hood is worn, and a thin elastic material over said cylindrically shaped device and extending over an area effective for covering the wearer's nostrils.

2. An emergency breathing hood as claimed in claim 1, wherein said nose blocking device has attached thereto an elastic cord means for engagement with the head of the wearer for supporting said nose blocking device in front of and in contact with the wearer's nostrils.

3. An emergency breathing hood as claimed in claim 2 which said hood has a transparent plastic strip attached at both its side edges to the inner surface of said hood, said elastic being slidably disposed between said strip and said hood.

* * * * *